(12) United States Patent
Ravikumar et al.

(10) Patent No.: US 8,216,165 B2
(45) Date of Patent: Jul. 10, 2012

(54) COMPRESSION GARMENTS WITH HEEL ELEVATION

(76) Inventors: Sundaram Ravikumar, Briar Cliff Manor, NY (US); Guy Osborne, Trumbull, CT (US); Vikram Ravikumar, Briar Cliff Manor, NY (US); Timothy J. Nolan, South Salem, NY (US)

( * ) Notice: Subject to any disclaimer, the term of this patent is extended or adjusted under 35 U.S.C. 154(b) by 24 days.

(21) Appl. No.: 12/911,563

(22) Filed: Oct. 25, 2010

(65) Prior Publication Data

US 2011/0087142 A1   Apr. 14, 2011

Related U.S. Application Data

(63) Continuation-in-part of application No. 11/356,692, filed on Feb. 17, 2006, now Pat. No. 7,909,787, and a continuation-in-part of application No. 11/494,720, filed on Jul. 27, 2006, now Pat. No. 7,967,766.

(60) Provisional application No. 60/730,766, filed on Oct. 27, 2005.

(51) Int. Cl.
*A61F 5/00* (2006.01)
(52) U.S. Cl. .......................................... 602/13; 602/27
(58) Field of Classification Search ................ 602/5, 13, 602/23, 26, 27; 128/882
See application file for complete search history.

(56) References Cited

U.S. PATENT DOCUMENTS

| | | |
|---|---|---|
| 3,939,829 A | 2/1976 | Spann |
| 3,946,451 A | 3/1976 | Spann |
| 4,013,069 A | 3/1977 | Hasty |
| 4,030,488 A | 6/1977 | Hasty |
| 4,054,129 A | 10/1977 | Byars et al. |
| 4,071,031 A | 1/1978 | Lowman |
| 4,186,738 A | 2/1980 | Schleicher et al. |
| 4,197,845 A | 4/1980 | Browning |
| 4,266,298 A | 5/1981 | Graziano |
| 4,320,746 A | 3/1982 | Arkans et al. |
| 4,399,815 A | 8/1983 | Bachorik |
| 4,402,312 A | 9/1983 | Villari et al. |
| 4,409,975 A | 10/1983 | Simhoni |
| D274,264 S | 6/1984 | Andersson |
| 4,730,610 A | 3/1988 | Graebe |
| 4,944,060 A | 7/1990 | Peery et al. |
| 4,977,891 A | 12/1990 | Grim |
| 5,085,214 A | 2/1992 | Barrett |
| 5,226,245 A | 7/1993 | Lamont |
| 5,328,445 A | 7/1994 | Spahn et al. |
| 5,412,822 A | 5/1995 | Kelly |

(Continued)

*Primary Examiner* — Michael A. Brown
(74) *Attorney, Agent, or Firm* — Edwards Wildman Palmer LLP; Scott D. Wofsy; Jason LaBerteaux

(57) ABSTRACT

A compression garment includes a backing member with a proximal end portion and opposed distal end portion. The backing member is configured to be disposed about at least a portion of a lower leg between calf and heel and has an inner surface to be disposed facing the lower leg, and an opposite outer surface. The garment further includes at least one compression bladder disposed within the backing member configured to compress at least a portion of the lower leg to augment venous return flow in the lower leg, an elevation member operatively coupled to the backing member and configured to elevate the heel from an underlying support surface and at least one support member disposed along a portion of the elevation member and along a portion of the backing member to retain the elevation member in a desired position with respect to the backing member to elevate the heel.

24 Claims, 14 Drawing Sheets

U.S. PATENT DOCUMENTS

| | | | |
|---|---|---|---|
| 5,431,624 A | 7/1995 | Saxton et al. | |
| 5,435,009 A | 7/1995 | Schild et al. | |
| 5,449,339 A | 9/1995 | Drennan | |
| 5,476,105 A | 12/1995 | Toth | |
| 5,489,259 A | 2/1996 | Jacobs et al. | |
| 5,666,681 A | 9/1997 | Meyer et al. | |
| 5,711,760 A | 1/1998 | Ibrahim et al. | |
| 5,765,564 A | 6/1998 | Ewing | |
| 5,839,139 A | 11/1998 | Fink | |
| 5,876,364 A | 3/1999 | Herbst | |
| 5,913,841 A | 6/1999 | Lamont | |
| 5,957,872 A | 9/1999 | Flick | |
| 5,957,874 A * | 9/1999 | Klein | 602/23 |
| 5,997,491 A | 12/1999 | Harris | |
| 6,001,119 A | 12/1999 | Hampson et al. | |
| 6,149,613 A * | 11/2000 | Klein | 602/23 |
| 6,151,739 A | 11/2000 | Meyer et al. | |
| 6,175,979 B1 | 1/2001 | Jackson | |
| 6,260,221 B1 | 7/2001 | Grabell et al. | |
| 6,290,662 B1 | 9/2001 | Morris et al. | |
| 6,351,863 B1 | 3/2002 | Meyer et al. | |
| 6,494,852 B1 | 12/2002 | Barak et al. | |
| 6,572,573 B1 * | 6/2003 | Klein | 602/23 |
| 6,589,194 B1 | 7/2003 | Calderon et al. | |
| 6,634,045 B1 | 10/2003 | DuDonis et al. | |
| 6,689,079 B2 | 2/2004 | Flick et al. | |
| 6,786,879 B1 | 9/2004 | Bolam et al. | |
| 6,789,284 B2 | 9/2004 | Kemp | |
| 6,877,178 B2 | 4/2005 | Chapman et al. | |
| 6,968,585 B2 | 11/2005 | Shaw | |
| 7,141,032 B2 | 11/2006 | Flam et al. | |
| 7,258,676 B2 | 8/2007 | Calderon et al. | |
| 7,354,411 B2 | 4/2008 | Perry et al. | |
| 7,909,787 B2 | 3/2011 | Ravikumar | |
| 7,967,766 B2 | 6/2011 | Ravikumar | |
| 2001/0016960 A1 | 8/2001 | Grabell et al. | |
| 2005/0070828 A1 | 3/2005 | Hampson et al. | |
| 2005/0107728 A1 | 5/2005 | Vetters et al. | |
| 2009/0260639 A1 | 10/2009 | Hsu et al. | |
| 2010/0087765 A1 | 4/2010 | Gainey | |
| 2010/0100017 A1 | 4/2010 | Maguina | |

* cited by examiner

COMPRESSION GARMENTS WITH HEEL ELEVATION

CROSS-REFERENCE TO RELATED APPLICATIONS

This application is a continuation-in-part of co-pending application Ser. No. 11/494,720, filed Jul. 27, 2006, and is also a continuation-in-part of co-pending application Ser. No. 11/356,692, filed Feb. 17, 2006. Application Ser. No. 11/494,720 is a continuation-in-part of co-pending application Ser. No. 11/356,692, each of which claims the benefit of provisional Application No. 60/730,766, filed Oct. 27, 2005. Each of these applications is incorporated by reference herein in its entirety.

BACKGROUND OF THE INVENTION

1. Field of the Invention

The present invention relates generally to compression systems for vascular therapy. More particularly, the present invention is directed to a compression garment that stimulates or assists venous and/or arterial blood flow and also prevents, treats, and/or relieves decubitus ulcers.

2. Description of Related Art

Various conventional compression devices are known for applying intermittent compressive pressure to a patient's limb Such devices employ a garment (e.g., a sleeve) having one or more inflatable chambers, with the garment configured to be disposed about a patient's limb (e.g., leg and/or foot) such that intermittent inflation of the chamber(s) causes increased pressure to be applied intermittently against the patient's limb, causing increased blood flow velocity, assisting venous return. In some of these devices, referred to as sequential compression devices, multiple (i.e., two or more) chambers disposed along the venous path are controllably inflated sequentially.

These types of devices are used to assist in a large number of medical indications, mainly for preventing deep vein thrombosis (DVT) or other vascular disorders, such as Pulmonary Artery Disease (PAD), reducing the occurrence of edemas, and facilitating wound healing. For instance, persons subject to extended periods of bed rest or inactivity (e.g., post-operative recovery) are often susceptible to DVT, which is a clotting of venous blood in the lower extremities and/or pelvis. This clotting occurs due to the absence of muscular activity (stasis) in the lower extremities, which is required to pump the venous blood. Such clotting may also occur due to a local vascular injury or a hypercoaguble state. The condition can be life-threatening if a blood clot migrates to the lung, resulting in a pulmonary embolus or otherwise interfering with cardiovascular circulation.

Typically, the compression devices are applied to the leg and/or foot when the patient is in the operating room or in the bed, and left in place until the patient ambulates fully or until the time of discharge. Hospitalized patients, when in bed for a prolonged period of time, have a tendency to form pressure ulcers. In many cases, the patient may already be predisposed to ulcer formation because of, for example, reduced circulation, and may require compressive therapy outside of a hospital. One of the places where the pressure ulcers frequently develop is the heel. More specifically, because of its thin layer of subcutaneous tissue between the skin and bone, the heel is the second most common site for pressure ulcer development (after the sacrum). Heel ulcers are costly and, if not treated promptly and properly, may lead to osteomyelitis and even limb amputation.

The conventional methods and systems have generally been considered satisfactory for their intended purpose. However, there is still an need in the art for compressive therapy devices that allow for improved prevention of heel ulcer formation for patients receiving compressive therapy. There also remains a need in the art for such devices that are easy to make and use. The present invention provides a solution for these problems.

SUMMARY OF THE INVENTION

The subject invention is directed to a new and useful compression therapy device with heel elevation. The invention also provides a method and apparatus for eliminating or otherwise reducing or mitigating pressure on an individual's heel while the leg is receiving compressive therapy.

In accordance with certain embodiments, a compression garment includes a backing member with a proximal end portion and opposed distal end portion. The backing member is configured to be disposed about at least a portion of a lower leg between calf and heel and has an inner surface to be disposed facing the lower leg, and an opposite outer surface. The garment further includes at least one compression bladder disposed within the backing member configured to compress at least a portion of the lower leg to augment venous return flow in the lower leg, an elevation member operatively coupled to the backing member and configured to elevate the heel from an underlying support surface and at least one support member disposed along a portion of the elevation member and along a portion of the backing member to retain the elevation member in a desired position with respect to the backing member to elevate the heel.

In certain embodiments, at least one support member is wedge-shaped to maintain at least some heel elevation even with the compression bladder deflated. The elevation member may include at least two substantially overlapping elevation sub-members each having an end thereof coupled to the distal end portion of the backing member. At least one of the elevation sub-members may also include at least one inflatable bladder. The elevation member may also include at least one elevation member inflatable bladder.

The compression garment can include at least one elevation member inflatable bladder disposed on the outer surface of the backing member. At least one elevation member inflatable bladder can be pneumatically coupled to the at least one compression bladder. It is also contemplated that in certain embodiments, at least one elevation member inflatable bladder is pneumatically independent from the at least one compression bladder. The at least one elevation member inflatable bladder can be apportioned into a plurality of pneumatically coupled regions separated by at least one baffle.

In accordance with certain embodiments, the at least one elevation member inflatable bladder includes a portion that extends longitudinally along the outer surface of at least a portion of the backing member that is disposed between the lower calf and the upper ankle with the garment disposed about the lower leg. The distal portion of the at least one elevation member inflatable bladder may include opposed lateral portions extending laterally from opposite lateral sides of the backing member with the garment disposed about the leg.

In certain embodiments, the at least one compression bladder forms a predetermined gradient pressure profile when the at least one bladder is filled. The at least one compression bladder can be a wedge-shaped bladder, a cone-shaped bladder, a disk-shaped bladder, a rectangular-shaped bladder, or any other suitable shape.

In accordance with certain embodiments, a compression garment includes a backing member with a proximal end portion and opposed distal end portion. The backing member is configured to be disposed about at least a portion of a lower leg between calf and heel and has an inner surface to be disposed facing the lower leg, and an opposite outer surface. The garment further includes at least one compression bladder disposed within the backing member configured to compress at least a portion of the lower leg to augment venous return flow in the lower leg. The garment further includes an inflatable elevation member operatively coupled to the backing member and configured to elevate the heel from an underlying support surface. A cushioning member is disposed along a portion of the elevation member to reduce heel pressure.

In accordance with an aspect of the present invention, a compression garment comprises a backing member configured to be disposed about at least a lower leg portion of an individual between the calf and heel region, the backing member having an inner surface to be disposed facing the leg, and having an opposite outer surface; at least one compression bladder disposed on the inner surface of the backing member; and an elevation member mechanically coupled to the backing member and configured such that when the backing member is disposed about at least the lower leg portion of the individual the elevation member is capable of elevating the heel from an underlying surface in the event that the lower leg portion is extended above the underlying surface.

The elevation member may comprise an inflatable bladder, which, in some implementations is pneumatically independent from each of the at least one compression bladder and, in some implementations is pneumatically coupled to at least one of the at least one compression bladder. The inflatable bladder may be disposed on the outer surface of the backing member, and may be deflatable.

In accordance with certain embodiments, a compression garment includes a backing member with a proximal end portion and opposed distal end portion. The backing member is configured to be disposed about at least a portion of a lower leg between calf and heel and has an inner surface to be disposed facing the lower leg, and an opposite outer surface. The garment further includes at least one compression bladder disposed within the backing member configured to compress at least a portion of the lower leg to augment venous return flow in the lower leg and an elevation member operatively coupled to the backing member and configured to elevate the heel from an underlying support surface.

In accordance with another aspect of the present invention, a compression garment comprises at least one compression chamber capable of being coupled to a fluid source and configured to inflate and apply pressure against at least a portion of an individual's limb in response to receiving a fluid input from the fluid source; and at least one inflatable elevation chamber configured to elevate at least a portion of the individual's limb when inflated. In some implementations, the individual's limb is a leg and the at least one inflatable elevation chamber is configured to elevate the individual's heel.

In accordance with yet another aspect of the present invention, a compression garment comprises means for applying compressive pressure against at least a portion of an individual's lower leg by expanding in response to receiving a fluid input; and means for elevating the individual's heel from an underlying surface in the event that the lower leg is rested on the underlying surface, wherein the elevating means and applying means are integrally coupled mechanically. In some implementations, the elevating means comprises at least one inflatable elevation chamber, and the applying means comprises at least one inflatable compression chamber. In some implementations, the elevating means is implemented as at least one of a fluid filled member that is not adapted for deflation, and a preformed non-fluid filled cushion member that is not adapted for deflation.

These and other features of the systems and methods of the subject invention will become more readily apparent to those skilled in the art from the following detailed description of the preferred embodiments taken in conjunction with the drawings.

BRIEF DESCRIPTION OF THE DRAWINGS

So that those skilled in the art to which the subject invention appertains will readily understand how to make and use the devices and methods of the subject invention without undue experimentation, preferred embodiments thereof will be described in detail herein below with reference to certain figures, wherein.

DETAILED DESCRIPTION OF THE PREFERRED EMBODIMENTS

Figure 1A:
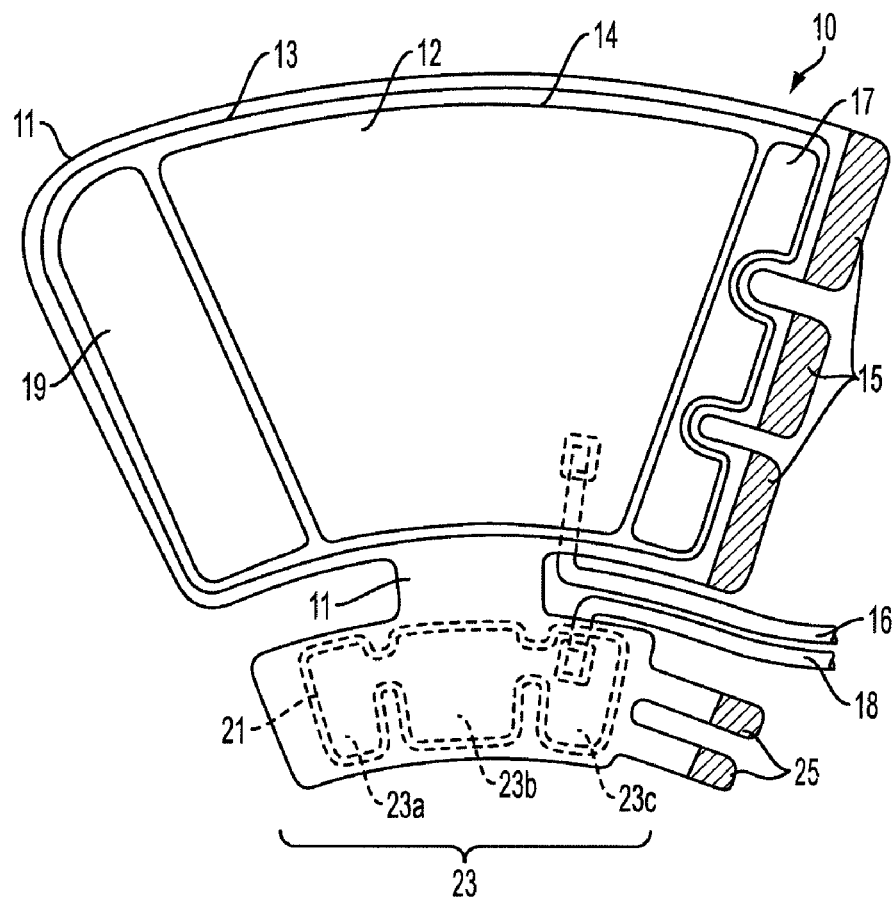
FIGS. 1A and 1B are interior and exterior plan views respectively, of a compression garment constructed in accordance with an exemplary embodiment of the present invention, showing a compression garment with heel elevation in the open position.
Figure 1B:
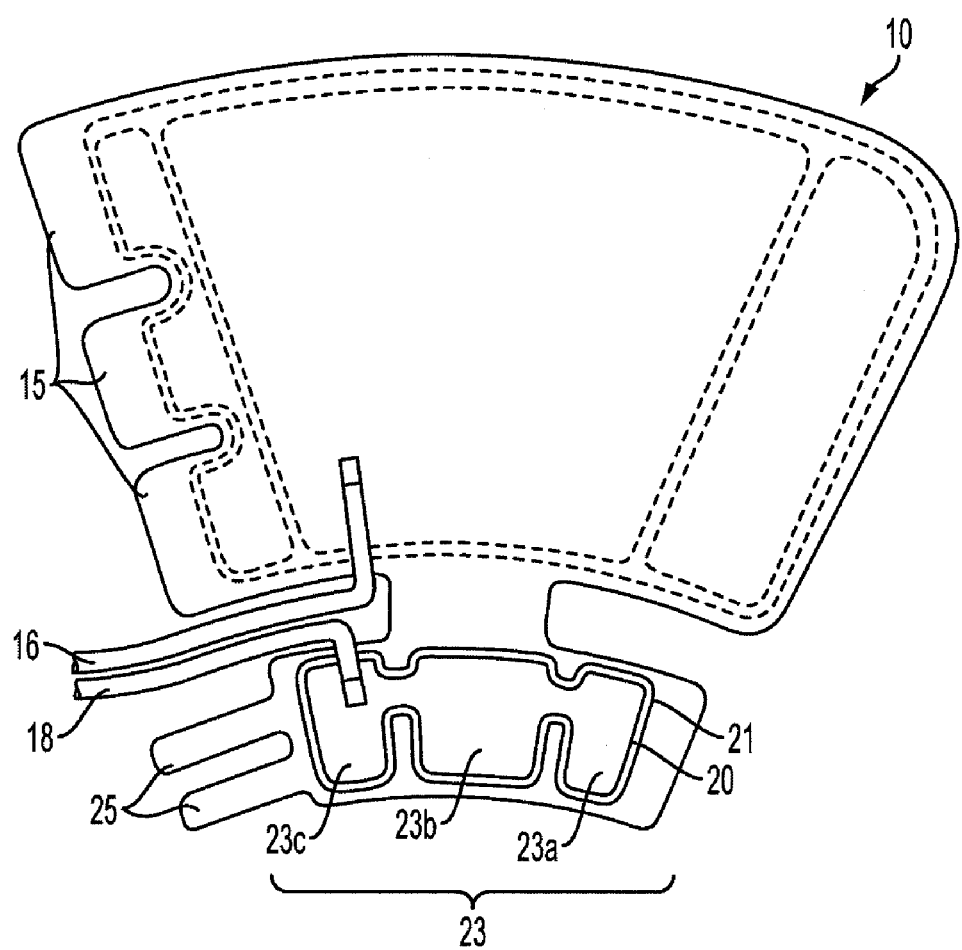

Reference will now be made to the drawings wherein like reference numerals identify similar structural features or aspects of the subject invention. For purposes of explanation and illustration, and not limitation, a partial view of an exemplary embodiment of the compression garment with heel elevation in accordance with the invention is shown in FIGS. 1A and 1B and is designated generally by reference character 10. Other embodiments of compression garments with heel elevation in accordance with the invention, or aspects thereof, are provided in FIGS. 2-22, as will be described.

The system of the invention can be used for attachment to the leg and/or foot to provide for compression therapy while also reducing or eliminating pressure on the heel region of the foot when the leg or foot is positioned such that the heel is in contact with an underlying surface (e.g., a bed) or would be in contact with an underlying surface but for the presence of the device. While embodiments of the present invention may be implemented to sufficiently elevate the foot to provide for spatial separation of the heel from an underlying surface that the heel would otherwise rest upon, embodiments of the present invention may also be advantageously used to reduce pressure on the heel even if the heel is in contact with an underlying surface. Additionally, even when the foot is cantilevered over the end of a bed or other supporting structure, embodiments of the present invention may be used to provide cantilever elevation and support, and to prevent or otherwise reduce pressure on the heel region as the individual moves the heel from a cantilevered position.

As also will be understood in view of the following description, embodiments of a compression treatment systems and methods of operation are discussed in terms of vascular therapy including a prophylaxis compression apparatus for application to a limb of a body and, more particularly, in terms of a compression treatment system having a controller that is adaptable for inflating thigh, calf, ankle and/or foot sleeves, and may also be configured for inflating one or more inflatable heel elevation bladders. A compression treatment system in accordance with various embodiments of the present invention includes a controller, interconnecting tubing, and at least one inflatable garment. The controller may include a pressure transducer, a manifold, and at least one output port adapted for fluidly coupling the controller to the at least one inflatable garment using interconnecting tubing. The at least one inflatable garment includes at least one inflatable bladder for providing compressive therapy to a patient's leg (e.g., thigh, calf, or ankle, or any combination thereof), and also includes at least one support member, which may include at least one inflatable bladder, for elevating the patient's heel. It is contemplated that a compression treatment system according to various embodiments of the present invention may be employed for preventing, alleviating, and/or treating conditions arising from patient immobility, such as deep vein thrombosis (DVT), peripheral artery disease (PAD), peripheral edema, decubitus ulcers, etc. It is contemplated that embodiments of compression treatment systems according to the present invention are not limited to any particular compression chamber configuration or pumping sequence, and include and are applicable to, for example, single chamber intermittent compression garments, as well as multi-chamber sequential compression garments. As used herein, intermittent compression garments or devices include sequential compression garments or devices; in other words, a sequential compression garment or device is considered to be a particular type of intermittent compression garment or device.

In the discussion that follows, the term "proximal" refers to a portion of a structure that is closer to a torso of a subject and the term "distal" refers to a portion that is further from the torso. Additionally, as used herein, the term "garment" is a generic term that includes, for example, foot cuff, knee sleeve, or leg sleeve, and is neither indicative of nor limited to any particular material, material properties, or construction techniques. In the present disclosure, the terms "chamber" and "bladder" are used interchangeably.

Referring now to FIGS. 1A and 1B, depicted are plan views of garment 10 according to an exemplary embodiment of a the present invention. More specifically, FIG. 1A is a plan view of garment 10 viewing the surface that contacts an individual's leg when garment 10 is in use ("the inner surface"), whereas FIG. 1B is a plan view of garment 10 viewing the surface opposite to the inner surface ("the outer surface"). The outer contour of garment 10 is configured so that garment 10 may be conformed about a patient's lower leg, extending from the ankle region and over the calf, with garment 10 being laterally wider towards the upper part of the leg (the proximal end) and tapering down towards the lower part of the leg (the distal end).

Garment 10 comprises three sheets 11, 13 and 20 of plastic (e.g., PVC) or similar material, with sheet 13 and sheet 20 being disposed on the inner surface and outer surface, respectively, of sheet 11. Different materials and/or laminations of materials may be used for sheets 11, 13, and 20, such as neoprene, rubber, polymer, resin, and/or fabric materials. It is noted that throughout the various plan views, dashed lines denote structural features that are disposed beneath the upper sheet or layer of the surface being viewed and may be disposed on the opposite side of the backing sheet relative to the side from which the garment is being viewed. It is contemplated that inner sheet 13 and outer sheet 20 are more elastic than the backing sheet 11, which in some embodiments may be relatively inelastic. Backing and inner sheets 11 and 13 are high-frequency welded together at their peripheries and internally in a pattern 14 defining an airtight inflatable/deflatable bladder 12 and non-inflatable, sealed chambers 17 and 19. Similarly, outer and backing sheets 20 and 11 are high-frequency welded together at their peripheries and internally in a pattern 21 defining an airtight inflatable bladder 23. As shown, the high frequency welds may be located internal to the periphery of garment 10 so that a hard edge consisting of the two material layers and weld joint is avoided. The high frequency welds may be replaced by any other suitable means for joining the materials, for example, ultrasonic welding, heat sealing, or adhesive bonding or the like.

As depicted, bladder 23 comprises three fluidly/pneumatically coupled compartments or sub-chambers 23a, 23b, and 23c. Sub-chambers 23a, 23b, and 23c are configured to facilitate chamber 23 wrapping about the ankle region. This configuration provides for bladder 23 to be disposed about the ankle region while bladder 12 is disposed along and about the calf region, the latter providing for intermittent calf compression while the former elevates the patient's heel.

Although bladder 12 is depicted as a single chamber inflatable bladder with a chamber having no internal weld pattern, it will be understood that bladder 12 may be implemented as a single chamber bladder having internal weld patterning, or having any other suitable internal pattern such as including baffling and/or seams provided by welding or otherwise joining materials 11 and 13 in a desired pattern, or as multi-chamber inflatable bladder, with each chamber possibly having an internal pattern. Additionally, garment 10 has non-inflatable sealed chambers 17 and 19, provided so that the softer more elastic material 20 contacts the skin during use. Such non-inflatable sealed chambers are advantageous, but optional. It is also possible that rather than bladder 23 being formed by joining (e.g., heat-welding) backing sheet 11 to sheet 20, a separately formed inflatable bladder may be attached (e.g., laminated) to backing sheet 11. Those skilled in the art will readily appreciate that implementations of the invention may include additional material layers without departing from the spirit and scope of the invention. A breathable polyester foam layer may be laminated to the inner surface of garment 10 to increase comfort, reduce moisture/perspiration, and/or mitigate chafing, rash formation, and/or skin breakdown for example.

As shown in FIGS. 1A and 1B, one edge of garment 10 has tabs 15 having hook pile fabric on the inner surface thereof to engage loop pile fabric provided at least along a portion of the outside surface of garment 10 along the opposite edge, to secure the sleeve in place on the leg. Similarly, tabs or straps 25 each include hook pile fabric on the inner surface thereof for engaging loop pile fabric provided on the outer surface of the distal section of garment 10 comprising bladder 23, to ensure that bladder 23 is maintained in position to provide proper and reliable heel elevation (e.g., despite patient movement). The hook and loop pile fabrics may be laminated (e.g., by adhesive or welding) to appropriate portions of garment 10. To secure the sleeve in place and/or to position/secure the elevation bladder, any of a variety of additional or other fastening mechanisms may be implemented, such as zippers, buttons, straps, laces, adhesive, etc. It is understood, however, that fastening mechanisms are not necessarily required for positioning and/or conforming the heel elevation bladder, and various embodiments of the present invention may be implemented which do not include fastening mechanisms and/or which provide for removably attachable fastening mechanisms (e.g., untethered straps with hook material provided at each end of one surface to engage loop material provided on the outer surface of the bladder). For example, the heel elevation bladder may be configured or contoured such that it conforms about the ankle region upon inflation and securing of the garment about the patient's leg.

Compression bladder 12 and elevation bladder 23 are provided with conduits or tubes 16 and 18, respectively, for coupling to one or more fluid sources (not shown) used for inflating these chambers. For example, an air compressor/pump (not shown) under control of a controller assembly (not shown) that regulates air flow and/or pressure coupled to bladder 12 and bladder 23 via tubes 16 and 18. The controller assembly may include one or more feeder/supply valves and/or one or more exhaust valves pneumatically coupled to the bladders and to the compressor/pump, one or more pressure transducers to sense the pressure supplied to one or more bladders and/or the compressive pressure applied against the leg by the bladder(s). The controller assembly can also include a programmable processor-based control unit that monitors the pressure sensors and controls the valves to provide desired inflation/deflation timing and pressure for the compressive bladder(s) (e.g., bladder 12 in FIG. 1A). The controller assembly may also be used to control inflation of one or more heel elevation bladders (e.g., bladder 23 in FIG. 1A). The one or more feeder/supply valves and/or exhaust valves may be implemented as solenoid valves and may be configured in a valve manifold, which may further include one or more of the pressure transducers, to provide a desired pneumatic circuit configuration to provide for controlled inflation and/or deflation of garment chambers. Any other suitable valving configuration can be used.

In operation, when the fluid source supplies compressed air to bladder 12 via tube 16, bladder 12 will inflate and apply sufficient pressure to the enclosed limb to augment venous return. An exhaust valve (e.g., in the pump manifold) may be opened, allowing the chamber to deflate via tube 16. The inflation and deflation rate, pressure, and duty cycle are appropriately controlled by the controller unit. In sequential compression garments, which include two or more separately-inflatable/deflatable and longitudinally disposed chambers, the controller unit also controls the relative inflation pressure and timing of the sequential chambers.

As indicated above, heel elevation bladder 23 may be pneumatically coupled via tube 18 (and, e.g., via a valve manifold) to the same controller unit and compressor/pump used for inflating/deflating bladder 12. In some implementations, heel elevation bladder 23 and bladder 12 may be coupled via respective tubes 18 and 16 to the fluid source via parallel and independent pneumatic circuits. In various implementations, heel elevation bladder 23 and bladder 12 may be alternately coupled via respective tubes 18 and 16 to the fluid source via a common pneumatic circuit path that is alternately connected to tubes 18 and 16 (e.g., using two valves synchronously switched 180 degrees out of phase). Accordingly, in this latter configuration, bladder 23 will be supplied with fluid pressure to inflate or maintain inflation during intervals that bladder 12 is deflated. It is also contemplated that bladder 12 may optionally include a one-way valve (e.g., attached to sheet 20 where tube 18 couples thereto, or in series with and along tube 18) to prevent deflation of heel elevation bladder 23 during intervals that the fluid source is connected to tube 16 and no fluid source is connected to tube 18.

It is contemplated that where two or more chambers are sequentially inflated to apply sequential compressive pressure to the patient, the pneumatic circuit and valve switch timing may be configured and controlled such that the fluid supply is alternately connected to each of the compressive bladders and the elevation bladder(s). In sequential compressive therapy implementations, two or more of the compression bladders may have independent pneumatic circuits coupled to the fluid source, and the heel elevation bladder(s) may be coupled to the fluid source via any one or more of these independent pneumatic circuits while each such pneumatic circuit is pneumatically disconnected from its associated compressive bladder (e.g., while that bladder is in a deflation state). In this way, independent pneumatic circuits supplying the compressive bladders may be multiplexed to supply one or more heel elevation bladders.

It is further contemplated that bladder 23 may be fluidly coupled via tube 18 to a separate fluid source (e.g., compressor) and controller. Heel elevation bladder 23 may also be inflated via a one-way valve, which, for example, may be attached directly to bladder 23 or pneumatically in series with tube 18.

Heel elevation bladder 23 need not be continuously or intermittently supplied by a fluid source during use. For example, heel elevation bladder 23 may be initially inflated using any inflation source, such as the pump/compressor used for intermittent inflation of bladder 12, a manual pump, a compressed air cylinder coupled to a regulator, etc.

After inflation, the inflation source may be disconnected from heel elevation bladder 23, which is provided with a sealable valve or a one way valve (e.g., affixed to bladder 23 or coupled thereto, e.g., via tube 18) to allow for retaining the fluid (e.g., air) within bladder 23 after the inflation source is disconnected and during patient use of garment 10. It may be advantageous for heel elevation bladder 23 to remain coupled to a fluid source to ensure that sufficient heel elevation is maintained during patient use of garment 10 for compressive therapy (which may be a prolonged time period), despite possible leakage from bladder 23.

Heel elevation bladder 23 may be deflated (e.g., after use, or when the patient wishes to ambulate without removing the garment). Deflation of heel elevation bladder 23 may be provided in various ways depending on the particular implementation; for example, deflation may be provided by any combination of one or more of the following: via an exhaust valve in the pump manifold, via bladder leakage, via an exhaust valve coupled to conduit 18, and/or via a separate releasable plug/valve (not shown) provided on the bladder 23, or in any other suitable manner.

Figure 2:
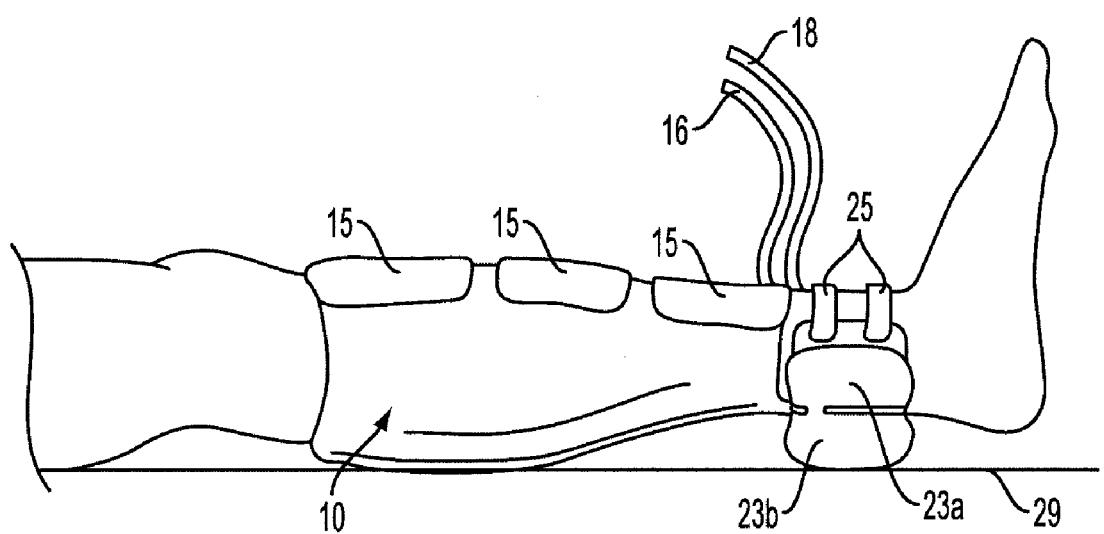
FIG. 2 is a side view of the compression garment of FIGS. 1A and 1B, showing the compression garment attached around an individual's leg.

Referring now to FIG. 2, depicted is a side view of garment 10 attached to a patient's leg, with heel elevation bladder 23 inflated, in accordance with an exemplary embodiment. The maximum displacement between the outer and inner surfaces of bladder 23 (i.e., when the bladder is fully inflated) is sufficient to elevate the patients heel such that the heel is spaced away from an underlying surface 29 (e.g., a bed), which surface the patient's heel would rest upon but for the elevation provided by heel elevation device 10. By way of example, such maximum displacement may be about two to four inches. It is understood, however, that even if the patient's heel or foot is cantilevered off the edge of an underlying surface (e.g., bed), heel elevation device 10 is still useful for preventing, for example, possible abrasions or shear, possible digging of the heels in the bed, heel pressure in the event the patient moves such that the foot or leg is no longer cantilevered, as well as for reducing or preventing pressure on the Achilles tendon and/or reducing or preventing other concentrated pressure that may affect circulation. Heel elevation bladder 23 is positioned at or near the ankle region, with bladder compartment 23b supporting the rear of the ankle and bladder compartment 23a disposed at the side of the ankle. Bladder 23 is inflated to a desired level of inflation (e.g., inflation pressure) to provide the desired heel elevation, cushioning/firmness, and/or stability. As will be appreciated, the elevation height may be adjustable, based on the volume (and hence pressure) of air pumped into the bladder.

The inelasticity (and semi-rigidity in some implementations) of backing 11 may also prevent or mitigate excessive inward pressure against the back of the leg as bladder 23 is inflated, which pressure could adversely affect circulation or control of compressive pressure, particularly in view of straps 25 securing the ankle support portion about the ankle. It is to be understood, however, that such prevention or mitigation of inward pressure by heel elevation bladder 23 is optional. In some configurations, at least a certain degree of inward inflation by heel elevation bladder 23 is advantageous for distributing the pressure over the back of the leg, conforming to the leg, and/or providing stable support (e.g., lateral support) for elevating the heel and reducing heel pressure.

As noted above, backing sheet 11 may be relatively inelastic; for example, backing sheet 11 may be sufficiently or substantially inelastic such that it does not substantially deform when garment 10 is attached in position to a patient's leg for compressive therapy and bladders 12 and 23 are inflated. As such, bladder 12 will primarily or predominantly expand against the patient's leg as it expands upon inflation, thereby predominantly and efficiently translating and coupling the inflation pressure as compressive pressure against the patient's leg. Also as such, with bladder 23 disposed on the outer surface of backing sheet 11 and backing sheet 11 being relatively inelastic, bladder 23 will primarily or predominantly expand in a posterior direction, outwardly and away from the patient's leg as it expands upon inflation, thereby avoiding unintended leg (e.g., ankle) compression that may adversely affect compressive therapy and/or adversely affect the patient (e.g., by decreasing blood flow).

It may be appreciated that when heel elevation bladder 23 segment of garment 10 is not configured to necessarily encircle the ankle region, the portion of backing sheet 11 that is disposed against heel elevation bladder 23 may be elastic (e.g., having the same elasticity as the outer facing elevation bladder material), as inflation of heel elevation bladder 23 will not necessarily apply compressive pressure against the patient's leg without heel elevation bladder 23 of garment 10 being secured about the leg (e.g., ankle). It is further contemplated that such a configuration may be provided by separately forming (i) the proximal portion of the garment comprising the upper compression bladder (e.g., corresponding to bladder 12 in FIG. 1A) by radio-frequency welding an elastic sheet and a substantially inelastic sheet, and (ii) the distal portion of the garment comprising the heel elevation bladder (e.g., similar to bladder 23 in FIG. 1A, but without an inelastic sheet) by radio-frequency welding two sheets of elastic material. Then, the proximal portion and distal portion may be welded together at their respective distal and proximal edges to form the completed garment.

Moreover, it may be understood that heel elevation bladder 23 may be implemented to function for both elevating the heel and applying intermittent compressive pressure (e.g., as part of a sequential compression device). For instance, with a garment constructed similarly to that described in the previous paragraph, heel elevation bladder 23 of garment 10 may be inflated to a baseline pressure sufficient to elevate the heel at a desired level, and then secured (e.g., using straps or extensions similar to straps 25 in FIGS. 1A and 1B) about the patient's lower leg (e.g., an de region) such that it does not apply excessive compressive pressure against the patient's leg at the baseline pressure. In operation, heel elevation bladder 23 may be controllably and intermittently (e.g., periodically, sequentially with one or more other bladders longitudinally disposed along the leg) inflated to a desired pressure above the baseline pressure to intermittently apply compressive pressure against the ankle region to assist venous return, with heel elevation bladder 23 being controllably deflated back to the baseline pressure for intervals between inflation cycles.

Figure 3:
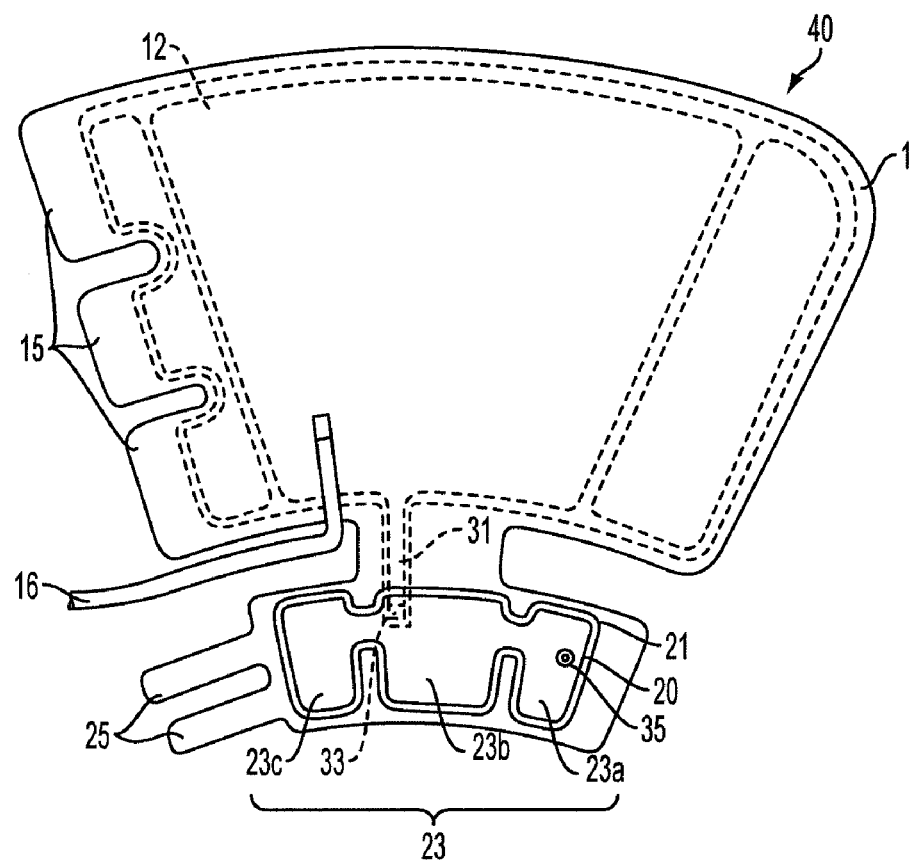
FIG. 3 is a plan view of another exemplary embodiment of a compression garment constructed in accordance with the present invention, showing a compression bladder pneumatically connected to an elevation bladder.

Referring now to FIG. 3, depicted is a plan view of the outer surface of garment 40 according to another exemplary embodiment. As shown, garment 40 is similar in construction to garment 10 depicted in FIGS. 1A and 1B. Bladder 23 is not inflated via a separate tube, but rather is pneumatically coupled to bladder 12 via lumen or tube 31 and a one-way valve 33, in which one-way valve 33 passes through or traverses backing sheet 11. Accordingly, upon controlled inflation of compressive bladder 12 via tube 16, bladder 23 will be inflated and maintained in an inflated state. Bladder 23 may include a pressure relief and/or exhaust valve 35 disposed through sheet 20 to ensure bladder 23 is not over-inflated and/or to deflate bladder 23 when desired. It will be understood that while lumen 31 is disposed on the inner surface of garment 40 and valve 33 traverses sheet 11 in the region of bladder 23, valve 33 could traverse sheet 11 within the region of bladder 12 with lumen 31 disposed on the outer surface of garment 40.

Figure 4:
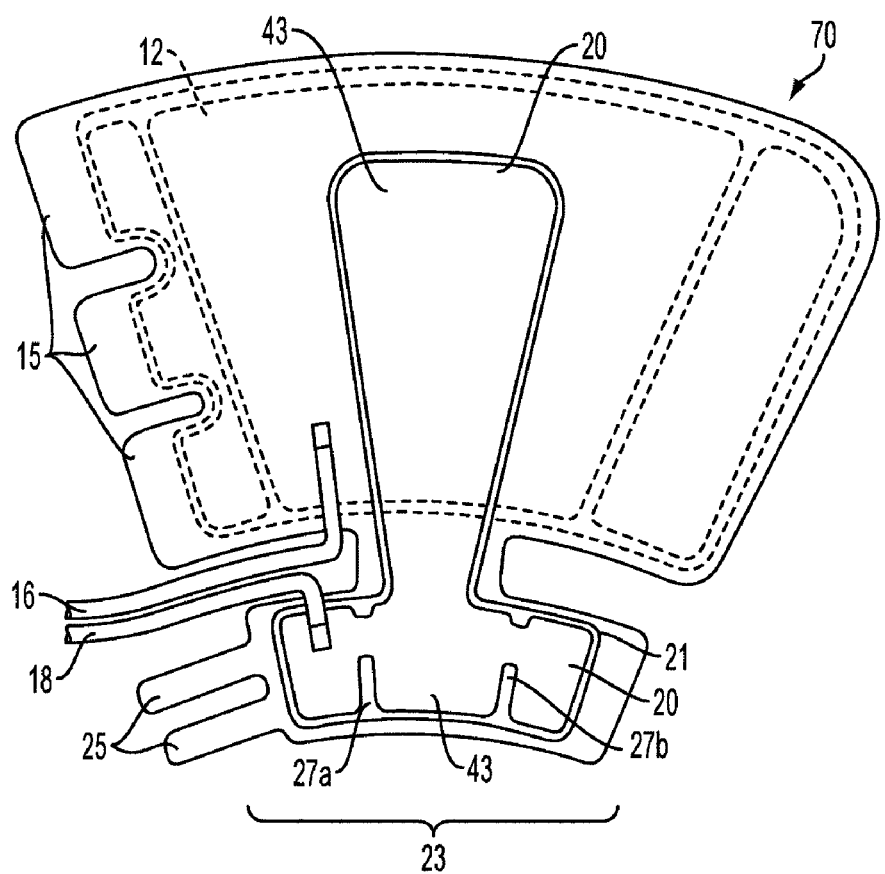
FIG. 4 is a plan view of another exemplary embodiment of a compression garment constructed in accordance with the present invention, showing a heel elevation bladder extended laterally across a compression garment.

Referring now to FIG. 4, depicted is a plan view of the outer surface of garment 70, in accordance with another exemplary embodiment of the present invention. As shown, garment 70 is similar in construction to garment 10; however, heel elevation bladder 43 is generally T-shaped, with a portion extending longitudinally along the outer surface of backing sheet 11 such that this longitudinal portion is disposed opposite to bladder 12 over a region that extends from approximately the mid-calf to the upper ankle when garment 70 is attached to a patient's leg. As shown, bladder 43 also includes a distal portion (similar to bladder 23) that extends laterally and is segmented by seams 27a and 27b and supports the ankle region when in use. Tube 18 is coupled into bladder 43 to provide for inflation thereof In various implementations, tube 18 may be eliminated, and bladder 43 may be pneumatically coupled to bladder 12, similar to the pneumatic coupling of compressive pressure and heel elevation bladders as depicted in FIG. 3.

Figure 5:
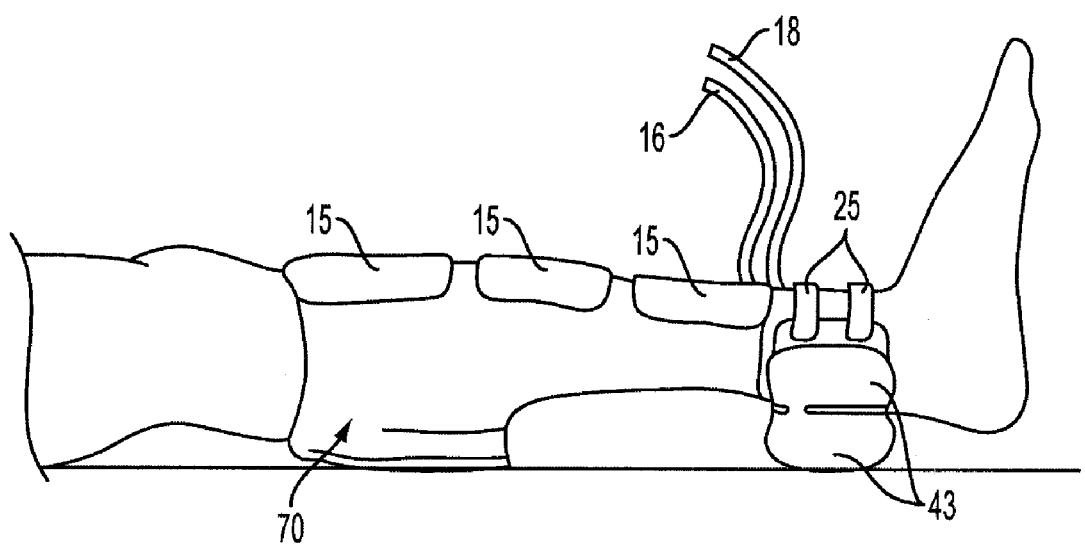
FIG. 5 is a side view of the compression garment of FIG. 4, showing the compression garment attached around an individual's leg.

Referring now to FIG. 5, depicted is a side view of garment 70 attached to a patient's leg, with heel elevation bladder 43 inflated, in accordance with an exemplary embodiment of the present invention. As may be understood from this side view, the cross sectional profile in the sagittal plane may have a generally trapezoidal, tapered shape that generally complements the contour of the adjacent rear leg portion such that the outer surface (posterior surface) of bladder 43 is generally parallel to the shin. It may also be understood that more than one separately inflatable posterior bladder may be provided along the length (longitudinally) between the proximal and distal ends. The cross sectional elevation profile in the sagittal plane (i.e., elevation along the longitudinal direction) may thus be adjusted by separately adjusting the pressure of each posterior bladder provided.

Elevation bladder (e.g. bladder 43) may be apportioned into multiple sections that are commonly inflated, but have different shapes or contain different volumes of fluid when the bladder is inflated. For instance, bladder 43 may be adapted to include multiple longitudinal and/or lateral sections by, for example, separating the sections with baffles or seams that may be formed by heat sealing or welding the outer surface of the bladder (i.e., sheet 20) to the inner surface (i.e., sheet 11) along most of the extent dividing adjacent sections, but leaving an opening (lumen) between adjacent sections such that fluid (e.g., air) can flow therethrough (as will be understood, a section of tubing or foam or other fluid-permeable membrane may be positioned within the opening(s) to prevent kinking from impeding airflow). Accordingly, upon inflation, each of the sections will be filled, but the shape/profile of each section may be determined by the baffle/seam configuration/shape and the fluid containing volume of each section separated by the baffles.

Figure 6:
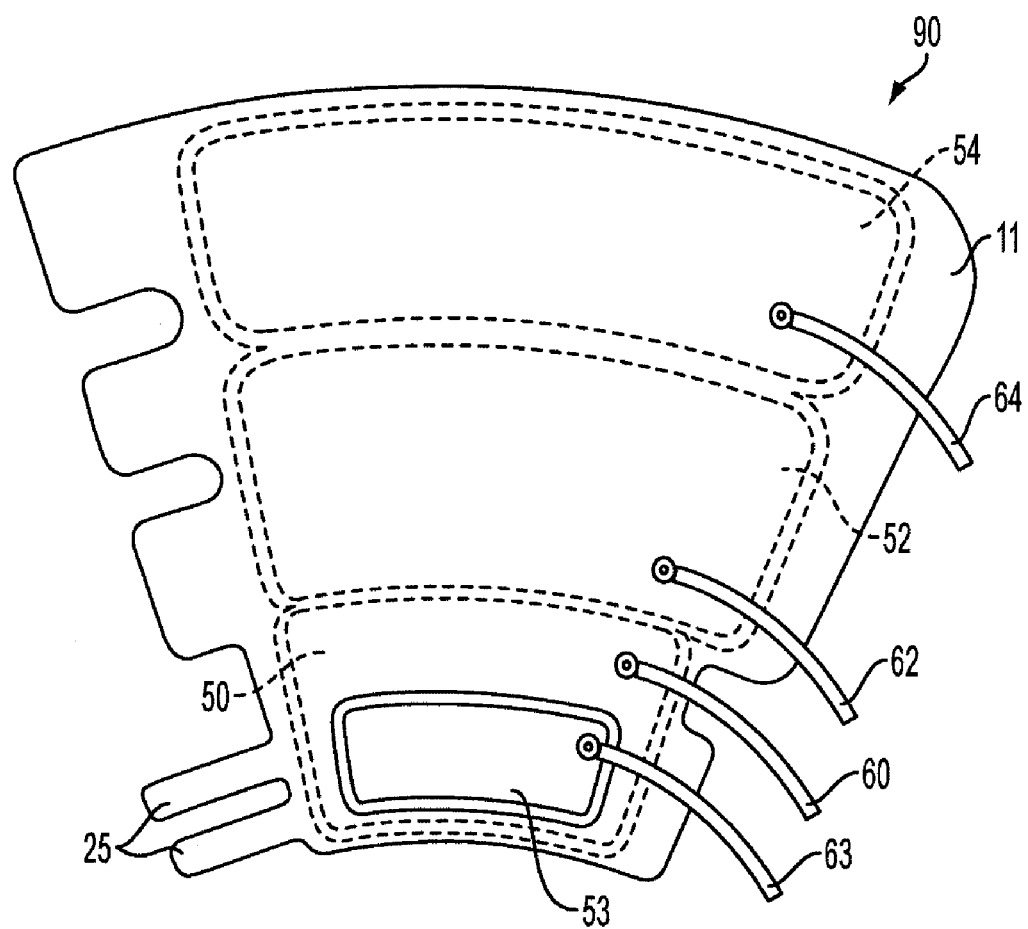
FIG. 6 is a plan view of another exemplary embodiment of a compression garment constructed in accordance with the present invention, showing multiple compression bladders with heel elevation.

With reference now to FIG. 6, depicted is a plan view of the outer surface of garment 90, in accordance with another exemplary embodiment of the present invention. As shown, garment 90 is generally similar in construction to garment 10; however, rather than providing a heel elevation bladder that is disposed distally relative to the compression chamber(s), the heel elevation bladder is oppositely opposed to a compression chamber. More specifically, garment 90 includes three pneumatically separate chambers, namely, upper-calf bladder 54 fluidly coupled to tube 64 for coupling to a fluid source, lower-calf bladder 52 fluidly coupled to tube 64 for coupling to a fluid source, and lower-leg/ankle bladder 50 fluidly coupled to tube 60 for coupling to a fluid source.

Additionally, as shown in FIG. 6, heel elevation bladder 53 is disposed on the outer surface of backing sheet 11 opposite to lower-leg/ankle bladder 50, and is fluidly coupled to tube 63 to provide for inflation thereof Bladder 53 may include baffles/seams (not shown) to, for example, facilitate a generally conforming bladder 53 about the ankle region when in use. In other implementations, tube 63 may be eliminated, and bladder 53 may be pneumatically coupled to bladder 50 (e.g., using a one-way valve through intervening sheet 11), similar to the pneumatic coupling of compressive pressure and heel elevation bladders in FIG. 3. Pneumatically separate chambers 50, 52, 54 may be controllably inflated and deflated to provide for sequential compression to augment venous return, as understood by those skilled in the art.

Appropriate orifices or pressure relief valves may be substituted for inflation tubes 62 and 64 (and associated ports/couplings into bladders 52 and 54), and bladders 50, 52, and 54 may be pneumatically coupled in series by restrictors such that these chambers are sequentially inflated upon inflation via tube 60, in accordance with compression devices described in US Patent Publication No. U.S. 2005/0070828 A1 to Hampson et al.

Figure 7:
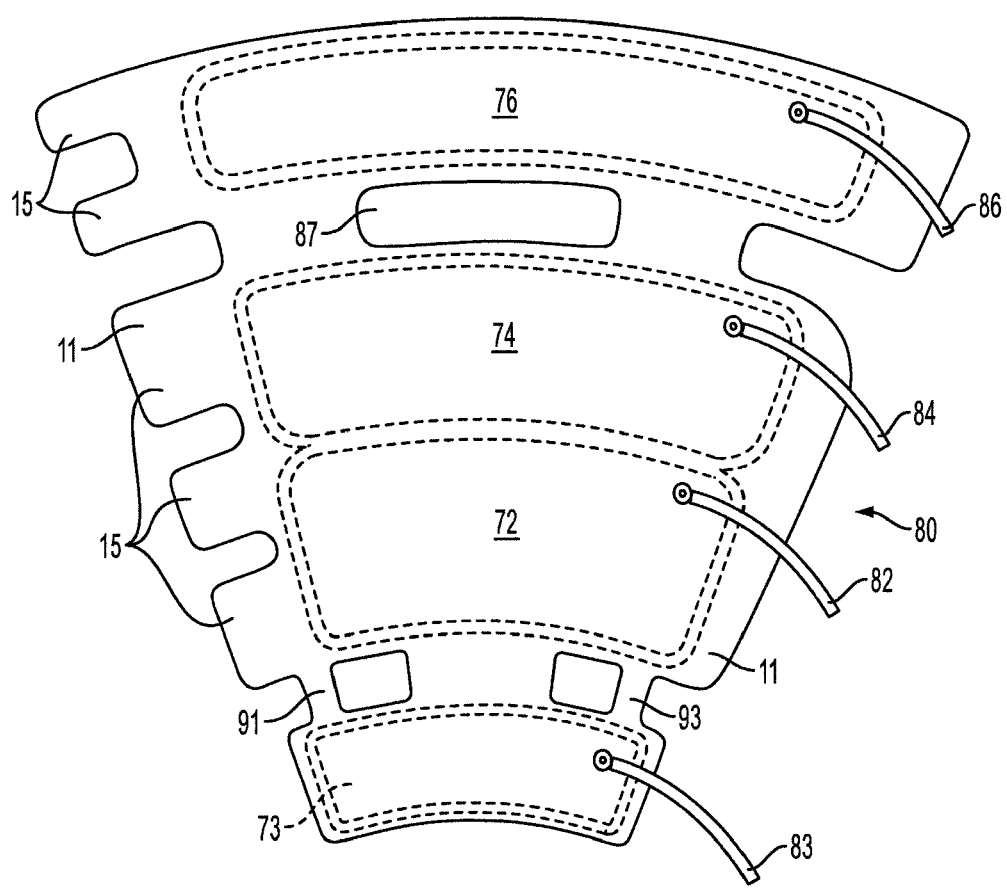
FIG. 7 is a plan view of another exemplary embodiment of a compression garment constructed in accordance with the present invention, showing a multiple compression bladder garment for an entire leg.

Referring now to FIG. 7, depicted is a plan view of the outer surface of garment 80, in accordance with another exemplary embodiment of the present invention. As shown, garment 80 is generally similar in construction to garment 90; however, garment 80 provides a thigh compression chamber, and also provides a heel elevation bladder 73 that is disposed distally relative (rather than partially or entirely opposite) to the compression chamber(s). More specifically, garment 90 includes three pneumatically independent chambers, namely, thigh-bladder 76 fluidly coupled to a tube 86 for coupling to a fluid source, upper-calf bladder 74 fluidly coupled to tube 84 for coupling to a fluid source, and lower-calf bladder 72 fluidly coupled to tube 82 for coupling to a fluid source.

Additionally, heel elevation bladder 73 is disposed distally with respect to the compression chambers, and is fluidly coupled to tube 83 to provide for inflation thereof. Backing sheet 11 includes an opening 87 to accommodate the knee when affixing the garment about a patient's leg. Segments 91 and 93 mechanically couple the lateral ends of the elevation bladder portion to the lateral ends of the compression bladder portion of garment 80, thus facilitating conformance of the heel elevation bladder about the ankle region (e.g., without additional straps wrapping around the ankle, such as straps 25 of FIGS. 1A and 1B). Segments 91 and 93 are each an integral part of sheet 11, but may be separate/discrete members attached (e.g., by radio-frequency welding) to sheet 11. Moreover, it is also contemplated that segments 91 and 93 could be the only mechanical coupling between the elevation bladder portion and the compression bladder portion of garment 80.

Figure 8:
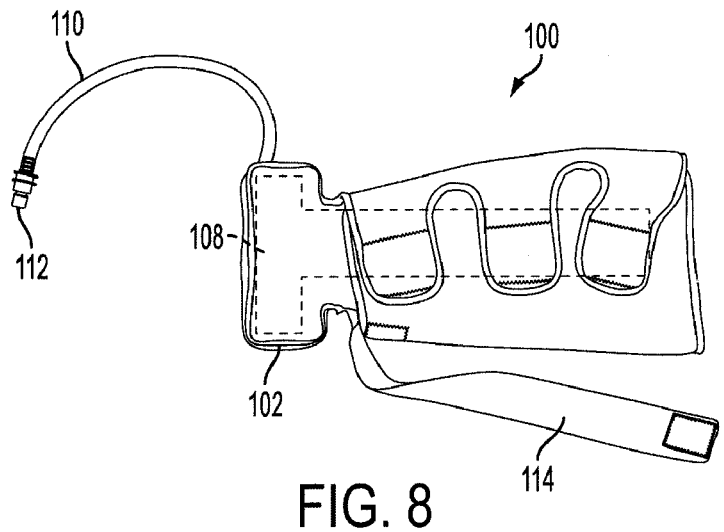
FIG. 8 is a top plan view of an exemplary embodiment of a compression garment constructed in accordance with the present invention, showing a heel elevation member with no ankle closure straps with the compression garment in the closed position as when attached to an individual's leg.
Figure 9:
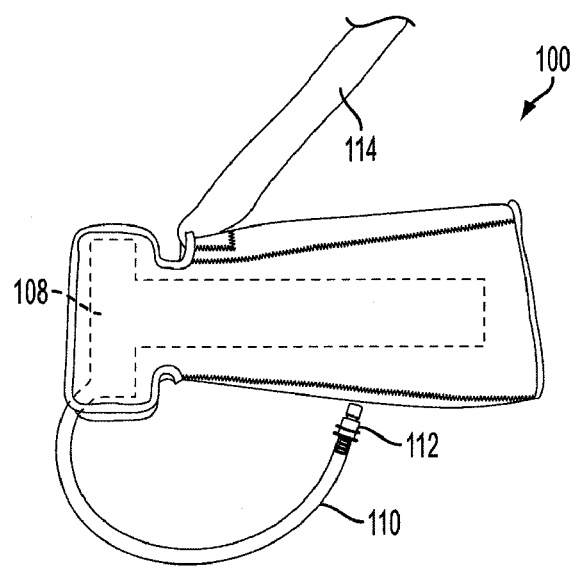
FIG. 9 is a bottom plan view of the compression garment of FIG. 8, showing the bottom of the heel elevation member and bladder placement.
Figure 10:
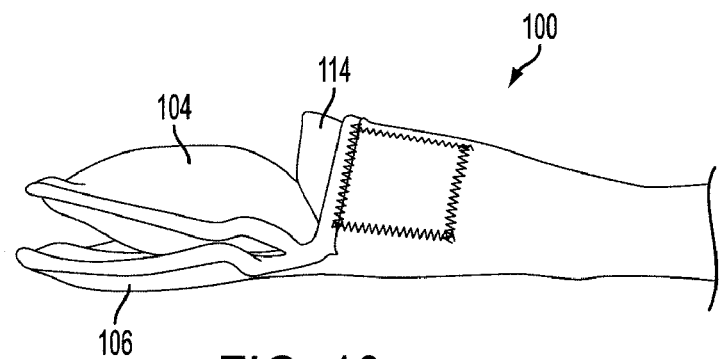
FIG. 10 is a side elevation view of a portion of the compression garment of FIG. 8, showing the elevation member deflated with no leg in the compression garment.

Referring now to FIGS. 8 and 9, another exemplary embodiment of a compression garment 100 is shown having a heel elevation member 102 with no ankle closure straps. Compression garment 100 has a heel elevation member 102 which include upper and lower heel elevation sub-members 104, 106 respectively, as seen in FIG. 10. Bladder 108 is depicted as a single bladder extending from heel elevation member 102 towards the proximal end of compression garment 100. Although bladder 108 is depicted as a single chamber inflatable bladder having no internal pattern, it will be understood that bladder 108 may be implemented as a single chamber bladder having internal patterning, for example, including baffling and/or seams provided by welding or otherwise joining materials 11 and 13 (not shown in FIG. 8, but see, e.g. FIG. 1) in a desired pattern. Bladder 108 may also be implemented as a multi-chamber inflatable bladder, with each chamber optionally having internal patterns.

Bladder 108 is provided with a tube 110 and connector 112 for coupling to one or more fluid sources (not shown) used for inflating bladder 108. A fluid (e.g., gas or liquid) source may be implemented as an air compressor/pump under control of a controller assembly that regulates air flow and/or pressure coupled to bladder 108 via tube 110.

With continued reference to FIG. 8, heel elevation member 102 is configured to be positioned under a portion of an individual's lower leg without straps like straps 25 shown in FIG. 1 attached around the lower leg or ankle. By not having heel elevation member 102 attached to the lower leg or ankle, improved user comfort and added mobility of the user's foot while compression therapy is administered can be achieved.

Figure 11:
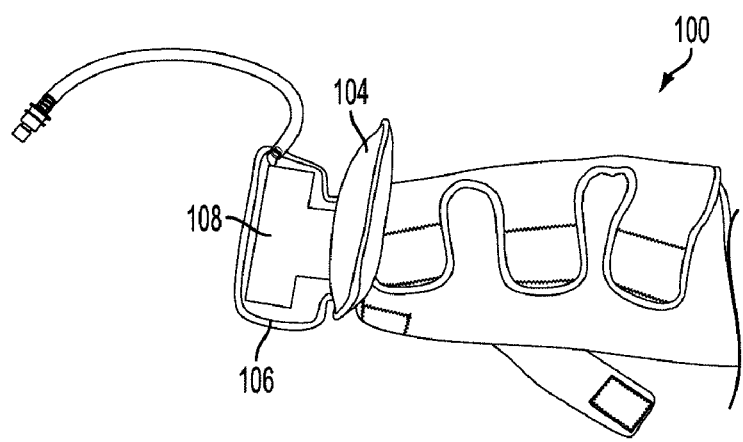
FIG. 11 is a top plan view of a portion of the compression garment of FIG. 8, showing the heel elevation member with the top elevation sub-member rotated to reveal the lower elevation sub-member and bladder placement.
Figure 12:
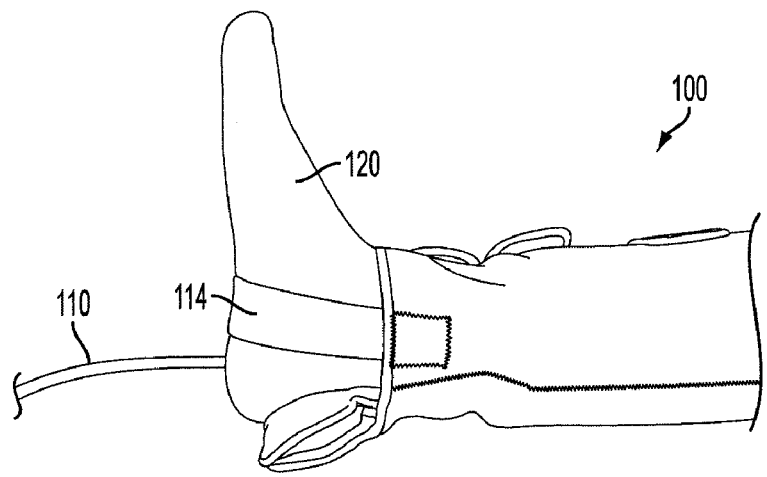
FIG. 12 is a side elevation view of a portion of the compression garment of FIG. 8, showing the compression garment attached around an individual's lower leg.

With reference now to FIG. 10, elevation sub-member 106 is shown deflated. FIG. 11 shows upper elevation sub-member 104 lifted to reveal lower elevation sub-member 106 which is constructed with bladder 108 incorporated for adjustable elevation of the heel. Upper elevation sub-member 104 is constructed with foam or other suitable material to provide reduced pressure to the heel while compression garment 10 is attached to a user and bladder 108 is not inflated as shown in FIG. 12. It is also possible that bladder 108 can be formed in both upper and lower elevation sub-members 104, 106 in any combination of single or multiple bladders as described above.

Referring again to FIG. 11, upper elevation sub-member 104 is shown as a foam member while bladder 108 is formed within lower elevation sub-member 106. Those skilled in the art will readily appreciate that bladder 108 or a separate bladder can be formed in upper elevation sub-member 104 to provide more heel elevation adjustability to improve user comfort and reduce and/or prevent the risk of formation of heel ulcers.

With reference to FIG. 12, compression garment 100 is shown attached around an individual's lower leg. Foot stirrup 114 is shown connected to compression garment 100 and disposed along the arch region of user's foot 120. Foot stirrup 114 may be used to provide added support to user's foot 120 during compression therapy to further reduce pressure on the heel and reduce and/or eliminate the risk of developing heel ulcers.

Figure 13:
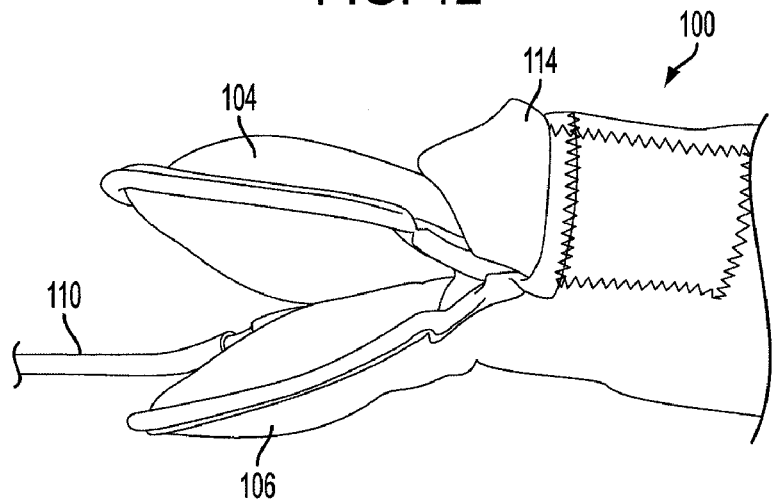
FIG. 13 is a side elevation view of a portion of the compression garment of FIG. 8, showing the elevation member inflated.

Referring now to FIG. 13, elevation member 106 is shown inflated without a user's foot on upper elevation member 104. It can be seen that the combination of upper elevation sub-member 104 and lower elevation sub-member 106 work in tandem to raise the heel with no ankle or foot compression.

Figure 14:
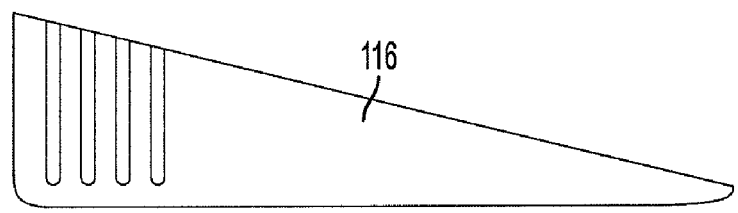
FIG. 14 is a side elevation view of a portion of an exemplary embodiment of a compression garment constructed in accordance with the present invention, showing a wedge-shaped support member.
Figure 15:
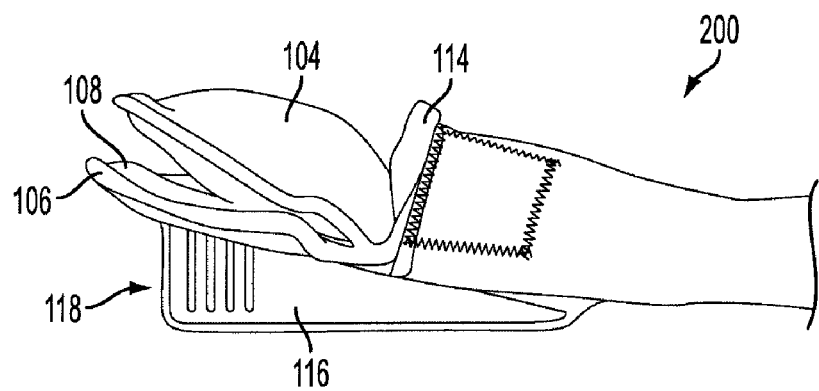
FIG. 15 is a side elevation view of a portion of the compression garment of FIG. 14, showing the wedge-shaped support member attached to the compression garment.
Figure 16:
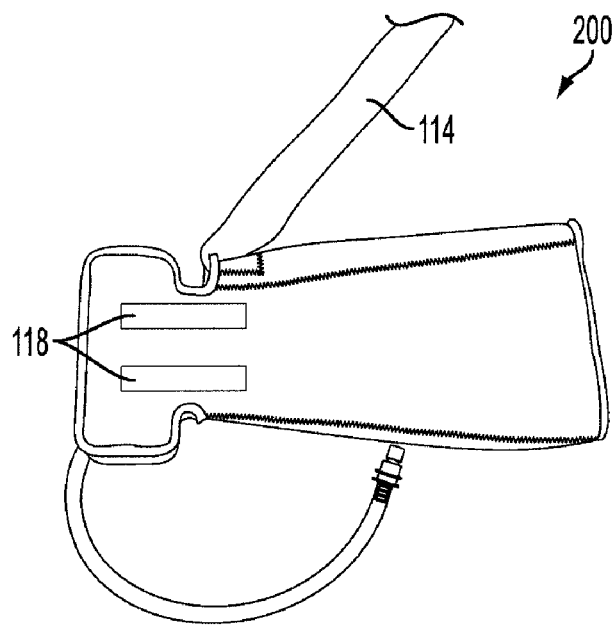
FIG. 16 is a bottom plan view of the compression garment of FIG. 14, showing the position of two sleeves, each for holding one wedge-shaped support member.

Referring to FIG. 14, a wedge-shaped support member 116 for use with another exemplary embodiment of a compression garment 200 is shown. FIG. 15 shows wedge-shaped support member 116 of FIG. 14 attached to compression garment 200. Wedge-shaped support member 116 attached to compression garment 10 can be used to maintain at least some heel elevation even with compression bladder deflated. Wedge-shaped support member 116 is retained by compression garment 200 through the use of sleeve 118. Wedge-shaped support member 116 is removable but could also be permanently attached to compression garment 200. FIG. 16 shows the placement position of two sleeves 118. Sleeves 118 can be used together with one or more support members 116 to retain elevation sub-members 104, 106 in a desired position with respect to backing member 11. It is also contemplated that support members 116 can be substantially flat rectangular semi-rigid support members constructed, for example, of a plastic material.

Figure 17:
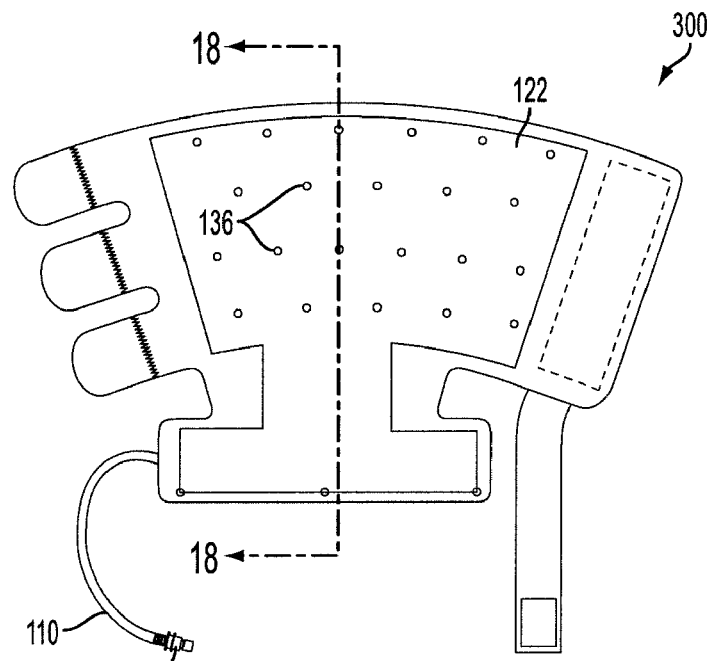
FIG. 17 is a top plan view of an exemplary embodiment of a compression garment constructed in accordance with the present invention, showing a compression bladder with a plurality of spot welds therein.
Figure 18:
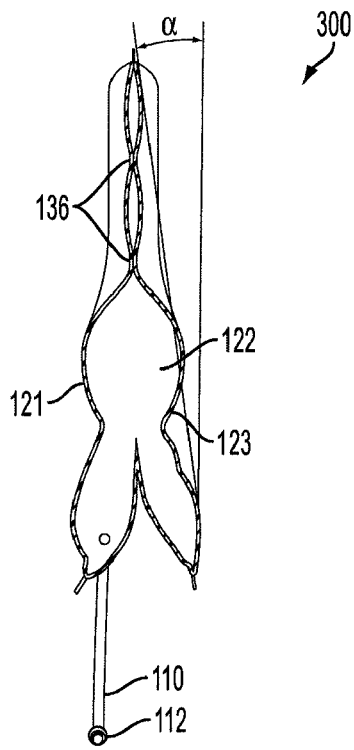
FIG. 18 is a cross-sectional view of the compression garment of FIG. 17 taken along line 18-18, showing the spot welds in the bladder joining the walls of the bladder to form a desired gradient profile.
Figure 19:
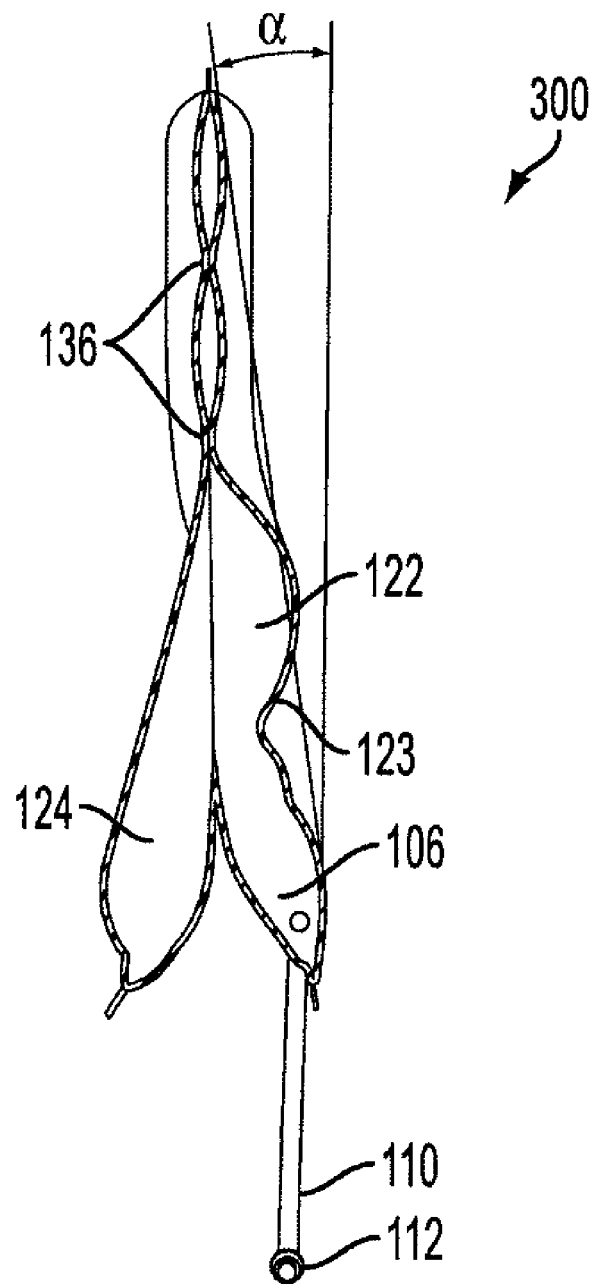
FIG. 19 is a cross-section view of the compression garment of FIG. 17 taken along line 18-18, showing the spot welds in the bladder joining the walls of the bladder to form a desired gradient profile in combination with a wedge-shaped foam member.

A number of different embodiments of bladders can be used in the compression garment of the subject invention such as those configurations described above. FIGS. 17 and 18 show compression garment 300 having bladder 122 with a plurality of spot welds 136 therein. Spot welds 136 are strategically placed within bladder 122 in a predetermined pattern based on the desired gradient profile, indicated in FIG. 18 as angle α, relative to the compression needed at the patient's treatment site. Spot welds 136 are strategically positioned to join first and second side walls 121 and 123 to one another. These spot welds 136 enable bladder 122 to change the gradient profile and take on a number of configurations when inflated. The geometric placement of spot welds 136 within bladder 122 allows increased inflation of certain portions of bladder 122, and can create one or more fluid chambers within bladder 122. This configuration is particularly useful when compression is needed to improve fluid movement (e.g., blood, lymph, etc.) within the body. Support members 116 can be of any other suitable shapes. FIG. 19 shows a compression garment with extended substantially wedge-shaped upper heel elevation sub-member 124. The extended wedge shape of upper heel elevation sub-member 124 is configured to raise user's foot 120 to at least reduce heel pressure with bladder 122 deflated and to enhance user comfort between compression intervals. Wedge-shaped upper heel elevation sub-member 124 can also work in combination with bladder 122 and spot welds 136 to provide a desired gradient profile relative to the compression needed at the patient's treatment site. Wedge-shaped upper heel elevation sub-member 124 can be of any other suitable shapes and made out of any suitable material, for example, foam or other conformable material. Wedge-shaped upper heel elevation sub-member 124 can also be combined with features of exemplary embodiments described above.

Figure 20:
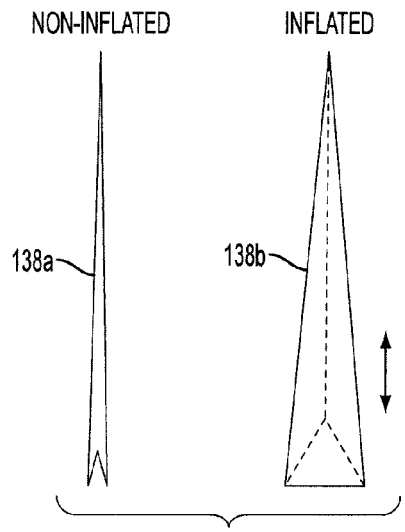
FIG. 20 is a schematic cross-sectional perspective view of a wedge-shaped bladder in a non-inflated state (left) and an inflated state (right)
Figure 21:
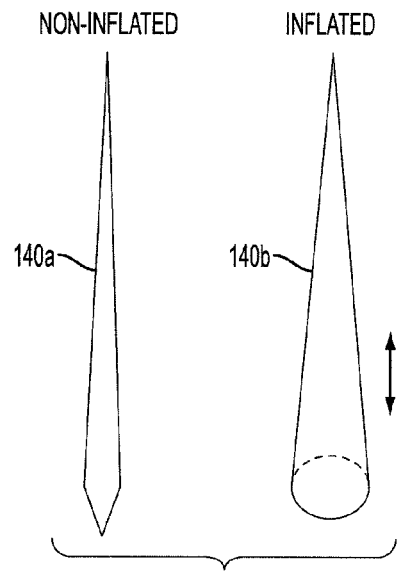
FIG. 21 is a schematic cross-sectional perspective view of a cone-shaped bladder in a non-inflated state (left) and an inflated state (right)

In addition to bladder 122 having spot welds 136 illustrated in FIGS. 17 and 18, several other bladder configurations shown in FIGS. 20-23 may be used within compression garments of the subject invention. FIG. 20 is a schematic cross-sectional view of a wedge-shaped bladder in a non-inflated state 138*a* (left) and an inflated state 138*b* (right) which may be used in compression apparatus 10 according to the subject invention. Wedge-shaped bladder 138*b* provides a comfortable and efficient gradient profile to the lower leg when inflated. Wedge-shaped bladder 138*b* has a pyramidal shape, as illustrated in FIG. 20 when inflated. Wedge-shaped bladder 138*b* advantageously accommodates the normal anatomy where the ankle is thinner than the lower leg. Thus, when wedge-shaped bladder 138*b* is placed on the leg, the thinner portion is positioned towards the knee and the thicker end is positioned towards the ankle. Referring now to FIG. 21, cone-shaped bladder 140*b*, is similar to wedge-shaped bladder 138*b*, and forms a cone when inflated. The inflated cone-shaped bladder 140*b* is also advantageous for use in normal anatomy in which the ankle is thinner than the lower leg.

Figure 22:
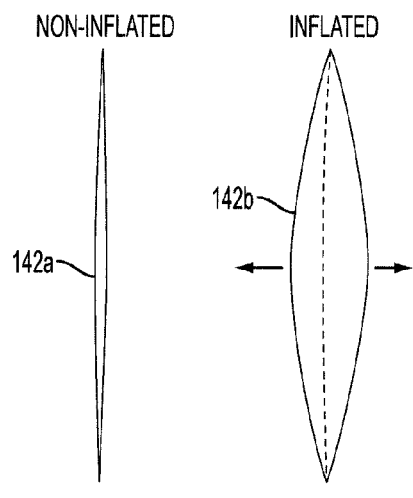
FIG. 22 is a schematic cross-sectional perspective view of a disk-shaped bladder in a non-inflated state (left) and an inflated state (right)
Figure 23:
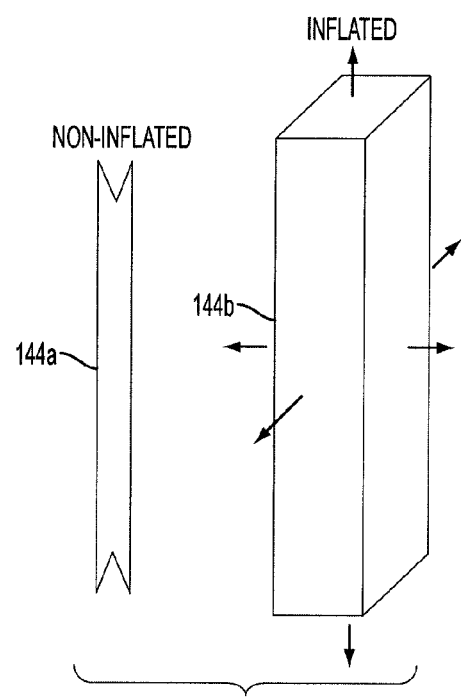
FIG. 23 is a schematic cross-sectional perspective view of a rectangular-shaped bladder in a non-inflated state (left) and an inflated state (right).

Turning to FIG. 22, a schematic cross-sectional view of a disk-shaped bladder in a non-inflated state 142*a* (left) and an inflated state 142*b* (right) is shown. Disk-shaped bladder 142*b* is formed from two walls and has a disk or saucer shape when inflated. Disk-shaped bladder 142*b* is also advantageous to provide more localized compression located approximately at the center of disk-shaped bladder 142*b*. Referring now to FIG. 23, a cross-sectional view of a rectangular-shaped bladder is shown. Rectangular-shaped bladder shown in a non-inflated state 144*a* (left) and an inflated state 144*b* (right) provides added benefits over disk-shaped bladder 142*b*. For example, rectangular-shaped bladder 144*b* is also known as a three-dimensional bladder that allows for compression without bulging or distention in a direction away from the treatment area. Rectangular-shaped bladder 144*b* inflates uniformly throughout its length and width. This uniform inflation reduces the bulging that may occur at the center of disk-shaped bladder 142*b* illustrated in FIG. 22. The walls of rectangular-shaped bladder 144*b* can be elastic or inelastic. It is also contemplated that a combination of both inelastic and elastic walls may be used. One or more portions of the walls of any of the shapes described in FIGS. 19-22 or other shapes may be formed of a rigid material or attached to a rigid material in order to avoid distention.

The present invention has been illustrated and described with respect to specific embodiments thereof, which embodiments are merely illustrative of the principles of the invention and are not intended to be exclusive or otherwise limiting embodiments. For instance, while in the foregoing embodiments, compressive therapy garments include integrally attached or formed bladders that are inflatable and deflatable, it will be understood that in implementations within the purview of the present invention, compressive therapy garments may alternately or additionally include integrally formed or attached (e.g., by adhesive, radio-frequency welding, etc.) heel elevation members that are not configured for inflation and/or deflation. For instance, such heel elevation members may be implemented using any of a variety of preformed and/or prefilled cushioning materials such as foam cushions and/or air, gel, or other fluid filled non-inflatable cushions, provided such heel elevation members provide sufficient elevation for mitigating and/or eliminating heel pressure. It is noted, however, that inflatable/deflatable bladders are well suited for providing adjustability of elevation and cushioning/firmness, as well as for evenly distributing/redistributing pressure and conforming to the patients leg, even under dynamic load conditions (e.g., resulting from patient movements that may change the load conditions). As yet a further illustrative example of variations within the purview of the present invention, more than one separately inflatable bladder may be provided in the posterior direction to allow variable height adjustment and cushioning pressure by selectively filling one or more bladders. Also, for example, while the foregoing embodiments illustrate heel elevation in connection with a calf and/or thigh compression chambers, other embodiments of the present invention may additionally include a foot compression chamber together with a heel elevation bladder. Further, while particular shapes, sizes, and materials have been described for purposes of illustration, it will be recognized that any of a variety of shape or size can be used, and the materials described are not exclusive but merely illustrative. Also, as noted above, while the bladder shown is inflated with air, it will be appreciated that any other fluid or medium such as liquid or gel can be used. Moreover, as also noted, it will be understood that bladders may be configured to have multiple pneumatically independent and/or pneumatically coupled bladder sections, and may also be configured to have various contours or lobulations.

The methods and systems of the present invention, as described above and shown in the drawings, provide for compression therapy with superior properties including improved heel elevation and support. While the apparatus and methods of the subject invention have been shown and described with reference to preferred embodiments, those skilled in the art will readily appreciate that changes and/or modifications may be made thereto without departing from the spirit and scope of the subject invention.

What is claimed is:

1. A compression garment, comprising:
   a backing member with a proximal end portion and opposed distal end portion, the backing member being configured to be disposed about at least a portion of a lower leg between calf and heel and having an inner surface to be disposed facing the lower leg, and an opposite outer surface;
   at least one compression bladder disposed within the backing member configured to compress at least a portion of the lower leg to augment venous return flow in the lower leg;
   an elevation member operatively coupled to the backing member and configured to elevate the heel from an underlying support surface, the elevation member including at least one inflatable bladder; and
   at least one support member disposed along a portion of the elevation member and along a portion of the backing member to retain the elevation member in a desired position with respect to the backing member to elevate the heel.

2. A compression garment as recited in claim 1, wherein the at least one support member is wedge-shaped to maintain at least some heel elevation even with the compression bladder deflated.

3. A compression garment as recited in claim 1, wherein the elevation member includes at least two substantially overlapping elevation sub-members each having an end thereof coupled to the distal end portion of the backing member.

4. A compression garment as recited in claim 3, wherein at least one of the elevation sub-members includes at least one inflatable bladder.

5. A compression garment as recited in claim 1, wherein at least one elevation member inflatable bladder is disposed on the outer surface of the backing member.

6. A compression garment as recited in claim 1, wherein at least one elevation member inflatable bladder is pneumatically coupled to the at least one compression bladder.

7. A compression garment as recited in claim 1, wherein at least one elevation member inflatable bladder is pneumatically independent from the at least one compression bladder.

8. A compression garment as recited in claim 1, wherein the at least one elevation member inflatable bladder is apportioned into a plurality of pneumatically coupled regions separated by at least one baffle.

9. A compression garment as recited in claim 1, wherein the at least one elevation member inflatable bladder includes a portion that extends longitudinally along the outer surface of at least a portion of the backing member that is disposed between the lower calf and the upper ankle with the garment disposed about the lower leg.

10. A compression garment as recited in claim 1, wherein the distal portion of the at least one elevation member inflatable bladder includes opposed lateral portions extending laterally from opposite lateral sides of the backing member with the garment disposed about the leg.

11. A compression garment as recited in claim 1, wherein a cushioning member is disposed along a portion of the elevation member to reduce heel pressure.

12. A compression garment as recited in claim 11, wherein the cushioning member is substantially wedge-shaped.

13. A compression garment as recited in claim 1, wherein the at least one compression bladder forms a predetermined gradient pressure profile when the at least one bladder is filled.

14. A compression garment as recited in claim 1, wherein the at least one compression bladder is selected from the group consisting of a wedge-shaped bladder, a cone-shaped bladder, a disk-shaped bladder and a rectangular-shaped bladder.

15. A compression garment, comprising:
a backing member with a proximal end portion and opposed distal end portion, the backing member being configured to be disposed about at least a portion of a lower leg between calf and heel and having an inner surface to be disposed facing the lower leg, and an opposite outer surface;
at least one compression bladder disposed within the backing member configured to compress at least a portion of the lower leg to augment venous return flow in the lower leg;
an inflatable elevation member operatively coupled to the backing member and configured to elevate the heel from an underlying support surface; and
a cushioning member disposed along a portion of the elevation member to reduce heel pressure.

16. A compression garment as recited in claim 15, wherein the garment includes at least one support member disposed along a portion of the elevation member and along a portion of the backing member and configured to retain the elevation member in a desired position with respect to the backing member to elevate the heel.

17. A compression garment as recited in claim 16, wherein the at least one support member is wedge-shaped to maintain at least some heel elevation even with the compression bladder deflated.

18. A compression garment as recited in claim 15, wherein the cushioning member is substantially wedge-shaped.

19. A compression garment as recited in claim 15, wherein the elevation member includes at least two substantially overlapping elevation sub-members each having an end thereof coupled to the distal end portion of the backing member.

20. A compression garment as recited in claim 15, wherein the inflatable elevation member is pneumatically independent from the at least one compression bladder.

21. A compression garment as recited in claim 15, wherein the inflatable elevation member is pneumatically coupled to the at least one compression bladder.

22. A compression garment as recited in claim 15, wherein the at least one compression bladder forms a predetermined gradient pressure profile when the at least one compression bladder is filled.

23. A compression garment as recited in claim 15, wherein the at least one compression bladder is selected from the group consisting of a wedge-shaped bladder, a cone-shaped bladder, a disk-shaped bladder and a rectangular-shaped bladder.

24. A compression garment, comprising:
a backing member with a proximal end portion and opposed distal end portion, the backing member being configured to be disposed about at least a portion of a lower leg between calf and heel and having an inner surface to be disposed facing the lower leg, and an opposite outer surface;
at least one compression bladder disposed within the backing member configured to compress at least a portion of the lower leg to augment venous return flow in the lower leg;
an elevation member operatively coupled to the backing member and configured to elevate the heel from an underlying support surface, wherein the elevation member includes at least one inflatable bladder.

* * * * *